US005965794A

United States Patent [19]
Turpen

[11] Patent Number: 5,965,794
[45] Date of Patent: *Oct. 12, 1999

[54] VIRAL AMPLIFICATION OF RECOMBINANT MESSENGER RNA IN TRANSGENIC PLANTS

[75] Inventor: Thomas H. Turpen, Vacaville, Calif.

[73] Assignee: Biosource Technologies, Inc., Vacaville, Calif.

[*] Notice: This patent is subject to a terminal disclaimer.

[21] Appl. No.: 08/336,724

[22] Filed: Nov. 9, 1994

Related U.S. Application Data

[63] Continuation of application No. 07/997,733, Dec. 30, 1992, abandoned.

[51] Int. Cl.⁶ .............................. A01H 5/00; C12N 15/40; C12N 15/83

[52] U.S. Cl. ...................... 800/288; 800/298; 800/317.3; 435/69.1; 435/235.1; 435/320.1; 435/468; 536/23.72

[58] Field of Search ........................ 536/23.72; 800/205, 800/288, 298, 317.3; 435/69.1, 70.1, 172.3, 235.1, 320.1, 468

[56] References Cited

FOREIGN PATENT DOCUMENTS

| | | |
|---|---|---|
| B7 195 191 | 3/1992 | Australia . |
| 067553 | of 0000 | European Pat. Off. . |
| 194809 | of 0000 | European Pat. Off. . |
| 278667 | of 0000 | European Pat. Off. . |
| A0 067 553 | 12/1982 | European Pat. Off. . |
| A0 425 004 | 5/1991 | European Pat. Off. . |
| A0 479 180 | 4/1992 | European Pat. Off. . |
| A0 573 767 | 12/1993 | European Pat. Off. . |
| 63-14693 | 1/1988 | Japan . |
| WOA89 08145 | 9/1989 | WIPO . |
| WOA90 12107 | 10/1990 | WIPO . |
| WOA91 13994 | 9/1991 | WIPO . |

OTHER PUBLICATIONS

Mori et al. 1991. J. Gen. Virol. 72(2):243–6.
Mori et al. 1992. J. Gen. Virol. 73(1):169–172.
Takamatsu et al. 1987. EMBO J. 6(2):307–311.
Hoffman et al. 1987. EMBO J. 6: 3213–3221.
Ahlquist, P., et al., *Viral Vectors,* Cold Spring Harbor Laboratory, New York, 183–189 (1988).
Ahlquist, P., and Pacha, R.F., *Physiol. Plant.* 79:163–167 (1990).
Butler, P.J.G., Mayo, M.A., Molecular architecture and assembly of tobacco mosaic virus particles, The molecular biology of the positive strand RNA viruses. (D. J. Rowlands, M.A. Mayo, and B.W.J. Mahy, eds.), Academic Press, London. pp. 237–257 (1987).
Cassidy, B., and Nelson, R., *Phytopathology* 80:1037 (1990).
Chapman, S., et al., Plant Journal 2:549 (1992).

Citovsky, V., Zambryski, P., *BioEssays* 13:373–379 (1991).
Culver, J.N., Lehto, K., Close, S.M., and Dawson, W.O., *Virology* (in press).
Dawson, W.O. and Hilf, M.E., *Ann. Rev. Plant Physiol. Plant Mol. Biol.* 43:527–555 (1992).
Dawson, et al., *Phytopahtol.* 78:783–789 (1988).
Dawson, W.O. et al., *Virology* 172:285–292 (1989).
Dawson, W.O., *Adv. Virus Res.* 38:307–342 (1990).
Dawson, W.O., *Virology* 186:359–367 (1992).
Deom, C.M., Lapidot, M., and Beachy, R.N., *Cell* 69:221–224 (1992).
Deom, C.M., Oliver, M.J., and Beachy, R.N., *Science* 237:389–394 (1987).
Dolja, V., et al., *PNAS* 89:10208 (1992).
Donson et al., *Proc. Natl. Acad. Sci.* 88:7204–7208 (1991).
Dunsmuir, P., Bond, D., Lee, K., Gidoni, D., and Towsend, J., Stability of introduced genes and stability of expression, *Plant molecular biology manual.* (S.B. Gelvin, R.A. Schilperoort, and D.P.S. Verma, eds.), Kluwer Academic Publishers, Dordrecht, The Netherlands, pp. C1:1–17 (1988).
French, R. et al., *Science* 231:1294–1297 (1986).
Horsch, R.B., Fry, J., Hoffmann, N., Neidermeyer, J., Rogers, S.G., and Fraley, R.T., Leaf disc transformation, *Plant molecular biology manual.* (S.B. Gelvin, R.A. Schilperoort, and D.P.S. Verma, eds.), Kluwer Academic Publishers, Dordrecht, The Netherlands, pp. A5:1–9 (1988).
Joshi, R.L., and Joshi, V., *FEBS Lett.* 281:1–8 (1991).
Joshi, R.L., et al., *EMBO J.* 9:2663–2669 (1990).
Jupin, I., et al., *Virology* 178:273–280 (1990).
Kearney, C. M., Donson, J., Jones, G. E., and Dawson, W. O., *Virology* 192:000–000 (1993) (in press).
Martelli, G.P., *Plant Disease* 76:436 (1992).
Ogawa, T., Watanabe, Y., Meshi, T., and Okada, Y., *Virology* 185:580–584 (1991).
Ow, D. W., et al., *Science* 234:856 (1986).
Potrykus, I., *Annual Rev. Plant Physiol. Plant Mol. Biol.* 42:205–225 (1991).

(List continued on next page.)

*Primary Examiner*—David T. Fox
*Attorney, Agent, or Firm*—Albert P. Halluin; John A. Bendrick; Howrey & Simon

[57] ABSTRACT

A novel method of over expressing genes in plants is provided. This method is based on the RNA amplification properties of plus strand RNA viruses of plants. A chimeric multicistronic gene is constructed containing a plant promoter, viral replication origins, a viral movement protein gene, and one or more foreign genes under control of viral subgenomic promoters. Plants containing one or more of these recombinant RNA transcripts are inoculated with helper virus. In the presence of helper virus recombinant transcripts are replicated producing high levels of foreign gene RNA.

Sequences are provided for the high level expression of the enzyme chloramphenicol acetyltransferase in tobacco plants by replicon RNA amplification with helper viruses and movement protein genes derived from the tobamovirus group.

21 Claims, 8 Drawing Sheets

OTHER PUBLICATIONS

Raffo A.J., and Dawson, W. O., *Virology* 184:277–289 (1991).

Rowlands, D.J., Mayo, M.A., and Mahy, B.W.J., eds., Academic Press, London. pp. 237–257 (1987).

Saito, T., Yamanaka, K., Okada, Y., *Virology* 176:329–336 (1990).

Shaw, W.V., Chloramphenicol acetyltransferase from chloramphenicol–resistant bacteria, *Methods in Enzymology*, vol. 53, (S. Fleischer and L. Packer, eds.), pp. 737–755 (1975).

Takamatsu, N., et al., *J. Virol.* 65:1619–1622 (1991).

Takamatsu, N., et al., *J. Virol.* 64:3686–3693 (1990).

Takamatsu, N., et al., *EMBO J.* 6:307–311 (1987).

Takamatsu, N., et al., *FEBS Letters* 269:73–76 (1990).

Turpen and Dawson, Transgenic Plants, Fundamentals and Applications, Marcel Dekkar, New York, pp. 195–217 (1992).

Turpen, T. H., Ph.D. Dissertation, University of California, Riverside, pp. 72–87 (1992).

Turpen, T., Ph.D. Dissertation, University of California, Riverside, pp. 106–132 (1992).

Turpen, T.H., and Dawson, W.O., Amplification, movement and expression of genes in plants by viral–based vectors, *Transgenic plants: fundamentals and applications* (A. Hiatt, ed.), Marcel Dekker, Inc., New York, pp. 195–217. (1992).

Van Haute, E., Joos, H., Maes, M., Warren, G., Van Montagu, M., and Schell, J., *EMBO J.* 2:411–417 (1983).

Velton and Schell, NAR 13:6981 (1985).

Walden and Schell, *Eur. J. Biochem.* 192:563–576 (1990).

Yamaya, J., Yoshioka, M., Meshi, T., Okada, Y., and Ohno, T., *Mol. Gen. Genet.* 211:520–525 (1988).

Zaitlin, M., Hull, R., *Ann. Rev. Plant Physiol.* 38:291–315 (1987).

Zambryski, P., Joos, H., Genetello, C., Leemans, J., Van Montagu, M., and Schell, J., *EMBO J.* 2:2143–2150 (1983).

Raffo, Anthony J. and Dawson, William O. "Constructon of Tobacco Mosaic Virus Subgenomic Replicons That Are Replicated and Spread Systemically in Tobacco Plants". *Virology* 184: 277–289 (1991).

Joshi, Rajiv L. et al. "BSMV genome mediated expression of a foreign gene in dicot and monocot plant cells". *The EMBO Journal*, vol.9: 2663–2669 (1990).

TRANSGENE (cDNA)

TRANSCRIPTION

TRANSCRIPT (RNA)

RNA PROCESSING AND RNA REPLICATION

REPLICON (RNA)

P = PROMOTER

5'RO = 5' REPLICATION ORIGIN

FG = SEQUENCE CODING FOR FOREIGN GENE AS WELL AS OTHER SEQUENCES. DOES NOT CODE FOR COMPLETE SET OF VIRAL REPLICATION PROTEINS REQUIRED FOR REPLICATION.

3' RO = 3' REPLICATION ORIGIN

TT = TRANSCRIPTION TERMINATION SEQUENCE

```
  1 guauuuuuacaacaauuaccaacaacaacaaacaacaaacaacauuacaauuacuauuua 60
 61 caauuacau AUG GCU CUA GUU GUU AAA GGA AAA GUG AAU AUC AAU     105
  1             M   A   L   V   V   K   G   K   V   N   I   N     12

106 GAG UUU AUC GAC CUG ACA AAA AUG GAG AAG AUC UUA CCG UCG AUG   150
 13  E   F   I   D   L   T   K   M   E   K   I   L   P   S   M    27

151 UUU ACC CCU GUA AAG AGU GUU AUG UGU UCC AAA GUU GAU AAA AUA   195
 28  F   T   P   V   K   S   V   M   C   S   K   V   D   K   I    42

196 AUG GUU CAU GAG AAU GAG UCA UUG UCA GAG GUG AAC CUU UUU AAA   240
 43  M   V   H   E   N   E   S   L   S   E   V   N   L   F   K    57

241 GGA GUU AAG CUU AUU GAU AGU GGA UAC GUC UGU UUA GCC GGU UUG   285
 58  G   V   K   L   I   D   S   G   Y   V   C   L   A   G   L    72

286 GUC GUC ACG GGC GAG UGG AAC UUG CCU GAC AAU UGC AGA GGA GGU   330
 73  V   V   T   G   E   W   N   L   P   D   N   C   R   G   G    87

331 GUG AGC GUG UGU CUG GUG GAC AAA AGG AUG GAA AGA GCC GAC GAG   375
 88  V   S   V   C   L   V   D   K   R   M   E   R   A   D   E   102

376 GCC ACU CUC GGA UCU UAC UAC ACA GCA GCU GCA AAG AAA AGA UUU   420
103  A   T   L   G   S   Y   Y   T   A   A   A   K   K   R   F   117

421 CAG UUC AAG GUC GUU CCC AAU UAU GCU AUA ACC ACC CAG GAC GCG   465
118  Q   F   K   V   V   P   N   Y   A   I   T   T   Q   D   A   132

466 AUG AAA AAC GUC UGG CAA GUU UUA GUU AAU AUU AGA AAU GUG AAG   510
133  M   K   N   V   W   Q   V   L   V   N   I   R   N   V   K   147

511 AUG UCA GCG GGU UUC UGU CCG CUU UCU CUG GAG UUU GUG UCG GUG   555
148  M   S   A   G   F   C   P   L   S   L   E   F   V   S   V   162

556 UGU AUU GUU UAU AGA AAU AAU AUA AAA UUA GGU UUG AGA GAG AAG   600
163  C   I   V   Y   R   N   N   I   K   L   G   L   R   E   K   177
                                    Origin of Assembly 601 AUU ACA AAC GUG AGA GAC GGA GGG CCC AUG GAA CUU ACA GAA GAA   645
178  I   T   N   V   R   D   G   G   P   M   E   L   T   E   E   192

646 GUC GUU GAU GAG UUC AUG GAA GAU GUC CCU AUG UCG AUC AGG CUU   690
193  V   V   D   E   F   M   E   D   V   P   M   S   I   R   L   207

691 GCA AAG UUU CGA UCU CGA ACC GGA AAA AAG AGU GAU GUC CGC AAA   735
208  A   K   F   R   S   R   T   G   K   K   S   D   V   R   K   222
```

MOVEMENT PROTEI

FIG. 6-2

```
 736 GGG AAA AAU AGU AGU AAU GAU CGG UCA GUG CCG AAC AAG AAC UAU  780
 233 G   K   N   S   S   N   D   R   S   V   P   N   K   N   Y    237

781 AGA AAU GUU AAG GAU UUU GGA GGA AUG AGU UUU AAA AAG AAU AAU  825
 238 R   N   V   K   D   F   G   G   M   S   F   K   K   N   N    252

826 UUA AUC GAU GAU GAU UCG GAG GCU ACU GUC GCC GAA UCG GAU UCG  870
 253 L   I   D   D   D   S   E   A   T   V   A   E   S   D   S    267

871 UUU UAA auacgcucgacgagauuuucaggagcuaaggaagcuaaa AUG GAG AAA  924
 263 F   *                                           M   E   K    3

925 AAA AUC ACU GGA UAU ACC ACC GUU GAU AUA UCC CAA UCG CAU CGU  969
   4 K   I   T   G   Y   T   T   V   D   I   S   Q   S   H   R    18

970 AAA GAA CAU UUU GAG GCA UUU CAG UCA GUU GCU CAA UGU ACC UAU 1014
  19 K   E   H   F   E   A   F   Q   S   V   A   Q   C   T   Y    33

1015 AAC CAG ACC GUU CAG CUG GAU AUU ACG GCC UUU UUA AAG ACC GUA 1059
  34 N   Q   T   V   Q   L   D   I   T   A   F   L   K   T   V    48

1060 AAG AAA AAU AAG CAC AAG UUU UAU CCG GCC UUU AUU CAC AUU CUU 1104
  49 K   K   N   K   H   K   F   Y   P   A   F   I   H   I   L    63

1105 GCC CGC CUG AUG AAU GCU CAU CCG GAA UUC CGU AUG GCA AUG AAA 1149
  64 A   R   L   M   N   A   H   P   E   F   R   M   A   M   K    78

1195 GUU UUC CAU GAG CAA ACU GAA ACG UUU UCA UCG CUC UGG AGU GAA 1239
  94 V   F   H   E   Q   T   E   T   F   S   S   L   W   S   E    108

1240 UAC CAC GAC GAU UUC CGG CAG UUU CUA CAC AUA UAU UCG CAA GAU 1284
 109 Y   H   D   D   F   R   Q   F   L   H   I   Y   S   Q   D    123

1285 GUG GCG UGU UAC GGU GAA AAC CUG GCC UAU UUC CCU AAA GGG UUU 1329
 124 V   A   C   Y   G   E   N   L   A   Y   F   P   K   G   F    138

1330 AUU GAG AAU AUG UUU UUC GUC UCA GCC AAU CCC UGG GUG AGU UUC 1374
 139 I   E   N   M   F   F   V   S   A   N   P   W   V   S   F    153

1375 ACC AGU UUU GAU UUA AAC GUG GCC AAU AUG GAC AAC UUC UUC GCC 1419
 154 T   S   F   D   L   N   V   A   N   M   D   N   F   F   A    168

1420 CCC GUU UUC ACC AUG GGC AAA UAU UAU ACG CAA GGC GAC AAG GUG 1464
 169 P   V   F   T   M   G   K   Y   Y   T   Q   G   D   K   V    183
```

```
     1465 CUG AUG CCG CUG GCG AUU CAG GUU CAU CAU GCC GUC UGU GAU GGC 1509
      184 L   M   P   L   A   I   Q   V   H   H   A   V   C   D   G   198

1510 UUC CAU GUC GGC AGA AUG CUU AAU GAA UUA CAA CAG UAC UGC GAU 1554
      199 F   H   V   G   R   M   L   N   E   L   Q   Q   Y   C   D   213

1555 GAG UGG CAG GGC GGG GCG UAA uuuuuuaaggcaguuauuggugcccuuaaac 1607
      214 E   W   Q   G   G   A   *                                   220
     1608 gccuggugcuacgccugaauaagugauaauaagcggaugaauggcagaaauucgucgagg 1667
     1668 guagucaagaugcauaauaaauaacggauugguccguaaucacacguggugcguacgau 1727
     1728 aacgcauaguguuuuucccuccacuuaaaucgaagggguugugucuuggaucgcgcgggguc 1787
     1788 aaauguauaugguucauauacauccgcaggcacguaauaaagcgaggggguucgaaucccc 1847
     1848 ccguuaccccccgguaggggccca                                      1870
```

VIRAL AMPLIFICATION OF RECOMBINANT MESSENGER RNA IN TRANSGENIC PLANTS

This is a continuation of application Ser. No. 07/997,733, filed Dec. 30, 1992, now abandoned.

BACKGROUND OF THE INVENTION

The present invention relates to the field of genetically engineering transgenic plants. More specifically, the invention relates to the use of viral RNA to achieve high level expression of foreign genes in plants.

The use of transgenic plants for high level expression of foreign genes has been targeted as an inexpensive means for mass producing desired products. All higher plants are photoautotrophic, requiring only $CO_2$, $H_2O$, $NO_3^{-1}$, $SO_4^{-2}$, $PO_4^{-3}$ and trace amounts of other elements for growth. From these inexpensive starting materials, plants are capable of synthesizing a variety of valuable products. Progress in utilizing transgenic plants as low cost factories will depend on both the characterization of biosynthetic pathways and on the further development of gene expression technologies.

In the past decade, a number of techniques have been developed to transfer genes into plants (Potrykus, I., *Annual Rev. Plant Physiol. Plant Mol. Biol.* 42:205–225 (1991)). For example, chromosomally integrated transgenes have been expressed by a variety of promoters offering developmental control of gene expression. (Walden and Schell, *Eur. J. Biochem.* 192:563–576 (1990)). This technology has been used primarily to improve certain agronomic traits such as disease resistance or food quality. (Joshi and Joshi, *Febs. Lett.* 281:1–8 (1991)). However, the utility of known transgene methodology is limited by 1) the difficulty of obtaining high level expression of individual transgenes 2) the lack of means necessary for coordinating control of several transgenes in an individual plant 3) the lack of means to enable precise temporal control of gene expression and 4) the lack of adequate means to enable shutting off introduced genes in the uninduced state (Walden and Schell, *Eur. J. Biochem* 192:563–576 (1990)).

The most highly expressed genes in plants are encoded in plant RNA viral genomes. Many RNA viruses have gene expression levels or host ranges that make them useful for development as commercial vectors. (Ahlquist, P., and Pacha, R. F., *Physiol. Plant.* 79:163–167 (1990), Joshi, R. L., and Joshi, V., *FEBS Lett.* 281:1–8 (1991), Turpen, T. H., and Dawson, W. O., Amplification, movement and expression of genes in plants by viral-based vectors, *Transgenic plants: fundamentals and applications* (A. Hiatt, ed.), Marcel Dekker, Inc., New York, pp. 195–217. (1992)). For example, tobacco (*Nicotiana tabacum*) accumulates approximately 10 mg of tobacco mosaic tombamovirus (TMV) per gram of fresh-weight tissue 7–14 days after inoculation. TMV coat protein synthesis can represent 70% of the total cellular protein synthesis and can constitute 10% of the total leaf dry weight. A single specific RNA transcript can accumulate to 10% of the total leaf mRNA. This transcript level is over two orders of magnitude higher than the transcription level observed for chromosomally integrated genes using conventional plant genetic engineering technology. This level of foreign gene expression has not yet been obtained using the prior art viral vectors in plants.

Most plant viruses contain genomes of plus sense RNA (messenger RNA polarity) (Zaitlin and Hull, *Ann. Rev. Plant Physiol.* 38:291–315 (1987)). Plus sense plant viruses are a very versatile class of viruses to develop as gene expression vectors since there are a large number of strains from some 22 plus sense viral groups which are compatible with a wide number of host plant species. (Martelli, G. P., *Plant Disease* 76:436 (1992)). In addition, an evolutionarily related RNA-dependent RNA polymerase is encoded by each of these strains. This enzyme is responsible for genome replication and mRNA synthesis resulting in some of the highest levels of gene expression known in plants.

In order to develop a plant virus as a gene vector, one must be able to manipulate molecular clones of viral genomes and retain the ability to generate infectious recombinants. The techniques required to genetically engineer RNA viruses have progressed rapidly. If the virus is an RNA virus, the virus is generally cloned as a cDNA and inserted into a plasmid. The plasmid is used to make all of the constructions. The genome of many plus sense RNA viruses can be manipulated as plasmid DNA copies and then transcribed in vitro to produce infectious RNA molecules (reviewed in Turpen and Dawson, Transgenic Plants, Fundamentals and Applications, Marcel Dekker, New York, pp 195–217 (1992)).

The interaction of plants with viruses presents unique opportunities for the production of complex molecules as typified by the TMV/tobacco system (Dawson, W. O., *Virology* 186:359–367 (1992)). Extremely high levels of viral nucleic acids and/or proteins accumulate in infected cells in a brief period of time. The virus catalyzes rapid cell-to-cell movement of its genome throughout the plant, with no significant tissue tropism. The infection is maintained throughout the life of the plant. The plants are not significantly adversely affected by the viral infection since the virus causes little or no general cytotoxicity or specific suppression of host gene expression.

The tobacco mosaic tobamovirus is of particular interest to the instant invention in light of its ability to express genes at high levels in plants. TMV is a member of the tobamovirus group. TMV virions are 300 nm×18 nm tubes with a 4 nm-diameter hollow canal, and consist of 2140 units of a single structural protein helically wound around a single RNA molecule. The genome is a 6395 base plus-sense RNA. The 5'-end is capped and the 3'-end contains a series of pseudoknots and a tRNA-like structure that will specifically accept histidine. The genomic RNA functions as mRNA for the production of proteins involved in viral replication: a 126-kDa protein that initiates 68 nucleotides from the 5'-terminus and a 183-kDa protein synthesized by readthrough of an amber termination codon approximately 10% of the time (FIG. 1). Only the 183-kDa and 126-kDa viral proteins are required for TMV replication in trans. (Ogawa, T., Watanabe, Y., Meshi, T., and Okada, Y., *Virology* 185:580–584 (1991)). Additional proteins are translated from subgenomic size mRNA produced during replication (reviewed in Dawson, W. O., *Adv. Virus Res.* 38:307–342 (1990)). The 30-kDa protein is required for cell-to-cell movement; the 17.5-kDa capsid protein is the single viral structural protein. The function of the predicted 54-kDa protein is unknown.

The minimal sequences required in cis for TMV replication are located at the extreme 5' and 3' noncoding regions (replication origins), as determined by analysis of deletion mutants in plant protoplasts (Takamatsu, N., et al., *J. Virol.* 64:3686–3693 (1990), Takamatsu, N., et al., *J. Virol.* 65:1619–1622 (1991)). In whole plants, helper-dependent RNA replicons, constructed by deletion of most of the 126/183-kDa replication protein sequence and most of the 30-kDa movement protein sequence, are replicated and spread systemically in the presence of wild type TMV (Raffo A. J., and Dawson W. O., *Virology* 184:277–289 (1991)).

Turpen, et al. discloses a simple and reliable gene transfer method wherein cDNA of TMV is engineered into *A. tumefaciens* for expression in plant cells (Turpen, T. H., Ph.D. Dissertation, University of California, Riverside, pp. 88–105 (1992)). This method provides an alternative to the use of synthetic infectious transcripts to inoculate plants based on host transcription of viral cDNA in vivo. Turpen showed successful transfection of tobacco (*N. tabacum* cv. Xanthi and Xanthi/nc) with wild type and defective viral genomes using this methodology.

Transfection also occurs spontaneously in transgenic lines containing defective or wild type cDNA of TMV integrated chromosomally (Turpen, T. H., Ph.D. Dissertation, University of California, Riverside, pp. 106–132 (1992), Yamaya, J., et al., *Mol. Gen. Genet.* 211:520–525 (1988)). Thus, once chromosomally integrated, viral replication can be derived from the process of host cell transcription.

Plant virus infections are initiated by mechanical damage to the plant cell wall. Following replication in the initially wounded cells, progeny viruses spread over short distances (cell-to-cell movement) before entering vascular tissue for long distance movement. Studies with chimeric tobamoviruses indicate that the coat protein is required for efficient long distance movement. However, a virus where the coat protein has been deleted or inactivated moves over short distances as does wild type virus (Dawson W. O. and Hilf, M. E., *Ann. Rev. Plant Physiol. Plant Mol. Biol.* 43:527–555 (1992)).

In the case of TMV, functional 30-kDa movement protein is absolutely required for cell-to-cell movement in whole plants, but can be deleted or inactivated without affecting replication in protoplasts or inoculated leaves (reviewed in Citovsky, V., Zambryski, P., *BioEssays* 13:373–379 (1991) and Deom, C. M., Lapidot, M., and Beachy, R. N., *Cell* 69:221–224 (1992)).

A sequence located within the 30 kDa movement protein gene of the U1 strain of TMV serves as the origin of assembly. It is at this origin of assembly that the TMV RNA and the viral capsid protein spontaneously aggregate to initiate the assembly of virions (Butler, P. J. G., Mayo, M. A., Molecular architecture and assembly of tobacco mosaic virus particles, The molecular biology of the positive strand RNA viruses. (D. J. Rowlands, M. A. Mayo, and B. W. J. Mahy, eds.), Academic Press, London. pp. 237–257 (1987)). A functional origin of assembly is also required for efficient long distance movement (Saito, T., Yamanaka, K., and Okada, Y., *Virology* 176:329–336 (1990)). There does not appear to be any additional requirements for packaging. A variety of heterologous sequences can be encapsidated yielding rod-shaped virions whose lengths are proportional to the size of the RNA molecule containing the origin of assembly (Dawson, W. O. et al., *Virology* 172:285–292 (1989)).

Construction of plant RNA viruses for the introduction and expression of foreign genes in plants is demonstrated by French, R., et al., *Science* 231:1294–1297 (1986); Takamatsu, N., et al., *EMBO J* 6:307–311 (1987); Ahlquist, P., et al., *Viral Vectors*, Cold Spring Harbor Laboratory, New York, 183–189 (1988); Dawson, W. O., et al., *Phytopathology* 78:783–789 (1988); Dawson, W. O., et al., *Virology* 172:285–292 (1989); Cassidy, B., and Nelson, R., *Phytopathology* 80:1037 (1990); Joshi, R. L., et al., *EMBO J.* 9:2663–2669 (1990); Jupin, I., et al., *Virology* 178:273–280 (1990); Takamatsu, N., et al., *FEBS Letters* 269:73–76 (1990); Japanese Published Application No. 63-14693 (1988); European Patent Application No. 067,553; and European Patent Application No. 194,809, European Patent Application No. 278,667. Most of the viral vectors constructed in these references were not shown to be capable of systemic movement in whole plants. Rather, gene expression has only been confirmed in inoculated leaves. In other cases, systemic movement and expression of the foreign gene by the viral vector was accompanied by rapid loss of the foreign gene sequence (Dawson, W. O., et al., *Virology* 172:285 (1989)).

With further improvements, successful vectors have been developed based on tobamoviruses for rapid gene transfer to plants. (Donson et al., *Proc. Natl. Acad. Sci.* 88:7204–7208 (1991)). For example, the α-trichosanthin gene was added to the genome of a tobamovirus vector under the transcriptional control of a subgenomic promoter obtained from a strain distantly related to wild type TMV (Turpen, T. H., Ph.D. Dissertation, University of California, Riverside, pp. 72–87 (1992)). This vector is an autonomous virus, containing all known viral functions. Two weeks post-inoculation, transfected *Nicotiana benthamiana* plants accumulated α-trichosanthin to levels of at least 2% total soluble protein. Purified recombinant α-trichosanthin produced by this method was correctly processed and had the same specific activity as the enzyme derived from the native source. Therefore, messenger RNA produced by viral RNA amplification in whole plants is fully functional. However, after prolonged replication of certain sequences using this vector, some genetic instability was observed primarily due to recombinational deletions and point mutations (Kearney, C. M., et al., *Virology* (in press)).

Recently, very similar results were obtained using gene vectors derived from additional plus sense RNA viruses infecting plants; a potyvirus, tobacco etch virus ((Dolja, V., et al., *PNAS* 89:10208–10212 (1992) and a potexvirus, potato virus X (Chapman, S., et al., Plant Journal 2:549–557 (1992)).

Therefore, the major functional disadvantages of existing prior art viral vectors are their genetic instability regarding the fidelity of maintenance of some non-viral foreign genes in systemically infected whole plants, after prolonged replication and passaging. For many products, it will be desirable to increase the genetic fidelity by lowering the proportion of deletion and other variants in amplified populations.

An additional concern regarding the use of viral vectors for the expression of foreign genes in transgenic plants is biological containment of the viral vectors encoding for foreign genes.

SUMMARY OF THE INVENTION

The instant invention provides a replicon derived from a chromosomally integrated transgene capable of expressing at least one foreign gene in plant cells. The replicon possesses replication origins with substantial sequence homology to a plus sense, RNA virus capable of infecting plants. The replicon is dependent for replication on a helper virus possessing trans-acting replication proteins where the replication proteins have substantial sequence homology to the replication proteins of a plus sense, RNA virus capable of infecting plants.

In still another aspect of the invention, the replicon additionally codes for a viral sequence upon which a helper virus is dependent in trans. In a yet further aspect of the present invention, the additional viral sequence coded for by the replicon is a viral movement protein.

In another aspect of the present invention, the replicon is also capable of moving the replicon-encoded genes away from the site of infection and is also capable of systemic expression.

The present invention also provides heterologous proteins and RNA sequences expressed in plants using one of the replicons of the instant invention.

The present invention also provides primary or secondary metabolites that accumulate in the tissues of a transfected plant as a result of the expression of a foreign gene product coded for by one of the replicons of the instant invention.

The present invention also provides transgenic plants that contain a chromosomally integrated transgene that codes for one of the replicons of the instant invention.

The present invention also provides a method for expressing a foreign gene in plants by integrating a transgene coding for one of the replicons of the instant invention into the host DNA of a plant cell and infecting the plant cell with a helper virus.

The present invention also provides a method for expressing a foreign gene in plants by integrating a transgene coding for one of the replicons of the instant invention into the host DNA of a plant cell and infecting the plant cell with a helper virus wherein the helper virus is dependent in trans on the replicon.

The present invention also provides a method for expressing a foreign gene in plants by integrating a transgene coding for one of the replicons of the instant invention into the host DNA of a plant cell and infecting the plant cell with a helper virus wherein the helper virus is dependent in trans on the replicon for expression of a movement protein.

In further embodiments of the present invention, expression of the foreign gene by the replicon is regulatable. In another, preferred embodiment of the replicon, the foreign gene sequence on the replicon is placed 5' to the 3' replication origin. In further preferred embodiments, the movement protein is derived from a tobamovirus and more specifically, a TMV strain virus.

BRIEF DESCRIPTION OF THE DRAWINGS

FIG. 6 is the sequence of the RNA replicon described in Example 1.

Definitions

Foreign gene: A "foreign gene" refers to any sequence that is not native to the virus.

In cis: "In cis" indicates that two sequences are positioned on the same strand of RNA or DNA.

In trans: "In trans" indicates that two sequences are positioned on different strands of RNA or DNA.

Movement protein: A "movement protein" is a noncapsid protein required for cell to cell movement of replicons or viruses in plants.

Origin of Assembly: An "origin of assembly" is a sequence where self-assembly of the viral RNA and the viral capsid protein initiates to form virions.

Replication origin: A "replication origin" refers to the minimal terminal sequences in linear viruses that are necessary for viral replication.

Replicon: A "replicon" is an arrangement of RNA sequences generated by transcription of a transgene that is integrated into the host DNA that is capable of replication in the presence of a helper virus. A replicon may require sequences in addition to the replication origins for efficient replication and stability.

Transcription termination region: The "transcription termination region" is a sequence that controls formation of the 3' end of the transcript. Self-cleaving ribozymes and polyadenylation sequences are examples of transcription termination sequences.

Transgene: A "transgene" refers to the DNA sequence coding for the replicon that is inserted into the host DNA.

Virion: A "virion" is a particle composed of viral RNA and viral capsid protein.

DETAILED DESCRIPTION OF THE INVENTION

The instant invention provides high level expression of foreign genes in plants by viral replicons wherein the replicons possess improved genetic stability. The replicons of the instant invention are produced in host plant cells by transcription of integrated transgenes. The replicons of the instant invention are derived, in part, from single stranded plus sense plant RNA viruses.

Figure 1:
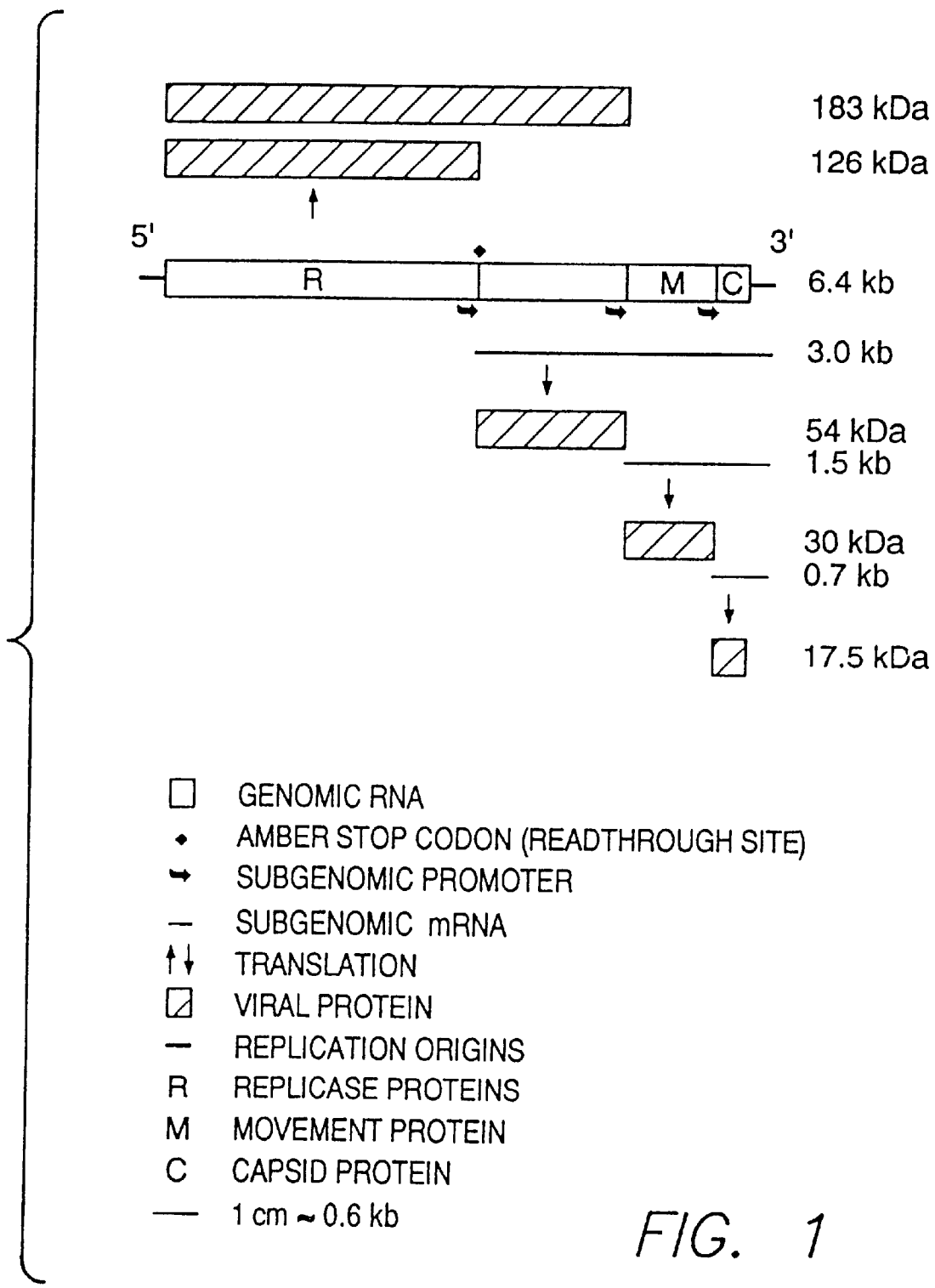
FIG. 1 depicts the genome of wild type TMV.
Figure 2A:
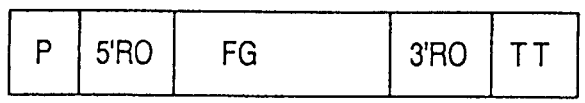
FIG. 2 depicts the essential features of the instantly claimed viral replicons.
Figure 2B:
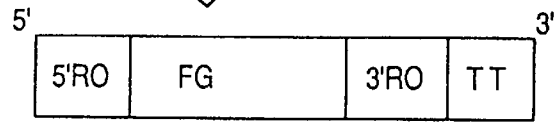
Figure 2C:
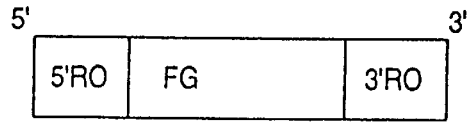

The replicons of the instant invention code for at least one foreign gene and possess sequences required in cis for replication ("replication origins"). FIG. 2(c). The replicons are produced by host cell transcription of a chromosomally integrated transgene to form an RNA transcript. The transgene is a DNA sequence that codes for the replicon and also contains a promoter and a transcription termination region. FIG. 2(a). The replicon is generated from an RNA transcript of the transgene by RNA processing and replication in the presence of a helper virus. FIG. 2(b).

The replicons of the instant invention lack functional replication protein sequences. Because the replicons of the instant invention lack replication protein sequences, they must rely on genetic complementation with helper viruses for replication. The replicon's dependency on the helper virus for replication enables regulatable amplification of these replicons through the introduction of the helper virus.

Genetic complementation of the replicon with a helper virus provides many advantages over autonomous viral vectors for amplifying gene expression. Each infected cell of a transgenic plant contains a correct master copy of the gene to be amplified. This reduces the effects of genetic drift in replicating RNA populations that can result in sequence instabilities and point mutations after prolonged replication of an RNA vector (Kearney, C. M., et al., *Virology* (in press)).

Figure 3:
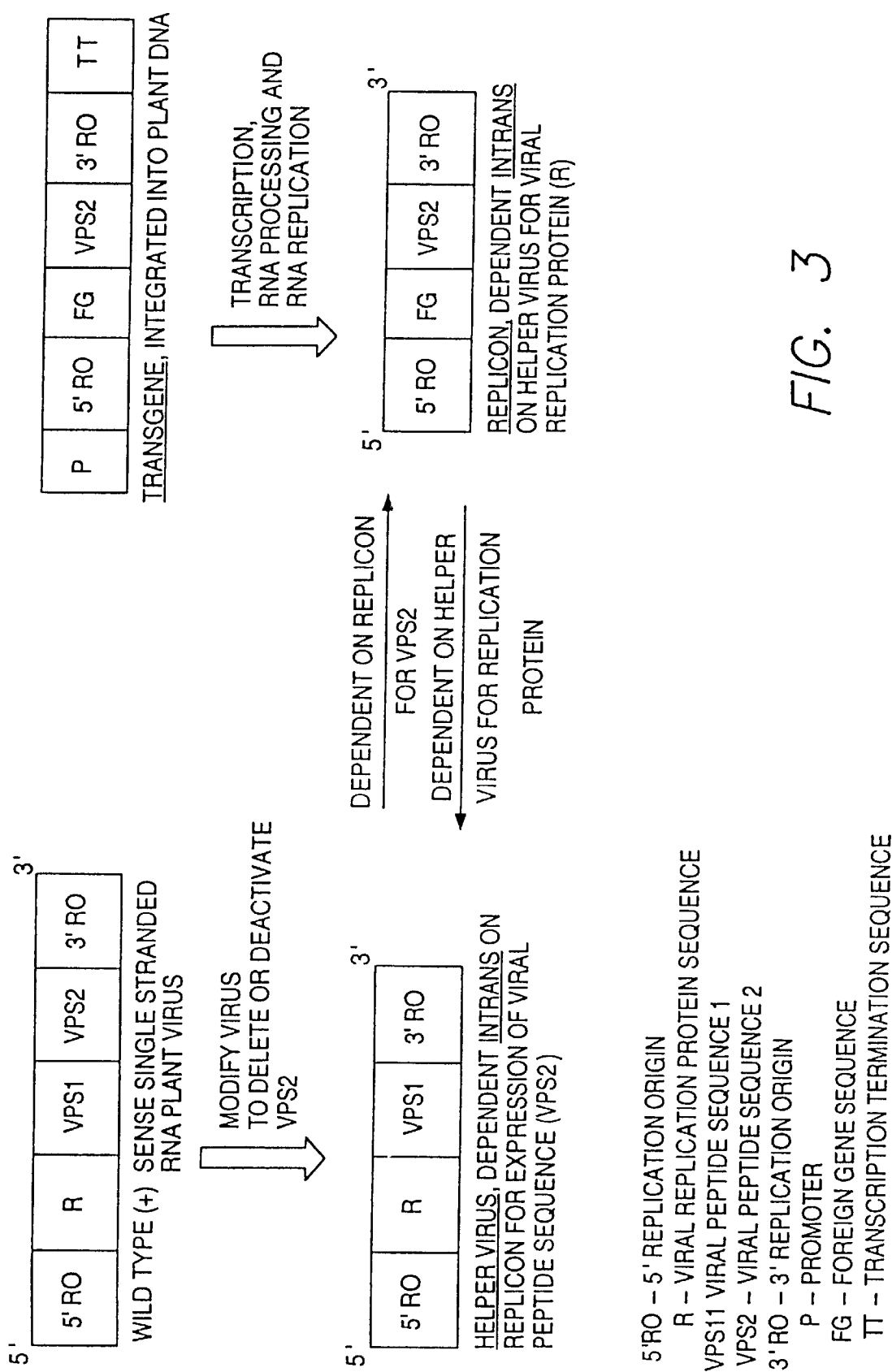
FIG. 3 depicts an embodiment where the replicon and helper virus are mutually dependent.
Figure 4:
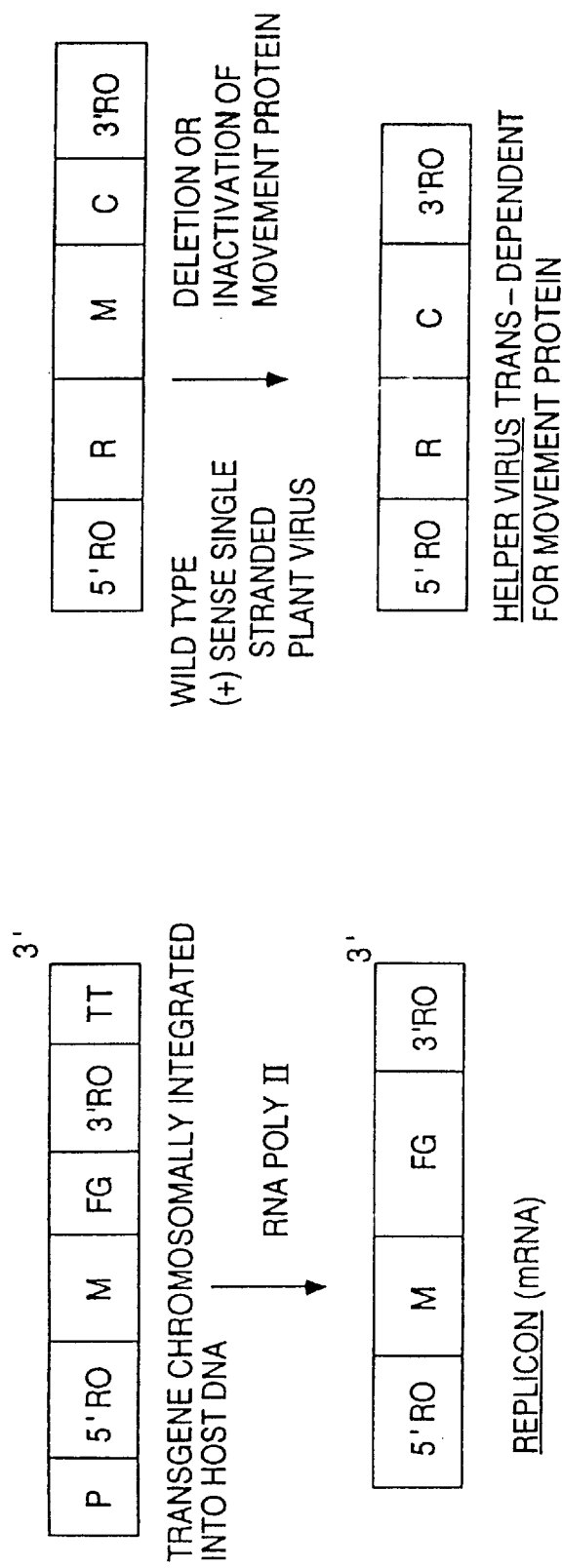
FIG. 4 depicts a preferred replicon gene arrangement where the foreign gene is situated at the 3' end of the genome 5' to the 3' replication origin.

In a further embodiment of the instant invention, the replicon codes for at least one sequence upon which the helper virus is dependent. Thus, in this further embodiment, the replicon and the helper virus are mutually dependent. [See FIG. 3]. Helper virus dependence on the replicon insures amplified expression of the replicon sequences by the helper virus in whole plants.

In a further embodiment, the replicon codes for a functional movement protein such as the 30 kDa TMV movement protein. The helper virus used in this embodiment does not possess a functional movement protein. Thus, the helper virus is dependent on the replicon for movement functionality. Movement proteins are necessary for cell to cell movement in plants. By placing a functional movement protein sequence on the replicon and either deactivating or deleting the same sequence on the helper virus or by using a host species with helper virus encoded movement protein incompatibility, the helper virus's dependency on the replicon enables systemic infection of the whole plant with the viral replicon plus helper virus.

This embodiment of the instant invention has the further advantage that the only virus released into the environment will be a debilitated helper virus. Thus, the helper virus will not be able to spread in plants that do not already contain a functional copy of the viral movement protein. This embodiment provides an option for more stringent levels of biological containment which may be desirable in some cases for large scale commercial production.

In a preferred embodiment, the replicon is formulated such that the sequences encoding the replication origins and the movement functions are linked to the foreign gene sequences. The chromosomally integrated transgene that codes for the replicon is transcribed by host RNA polymerase II producing recombinant mRNAs. In the presence of a helper virus, these transcripts are replicated as additional replicon components in a mixed population. During viral replication, subgenomic messenger RNA may be produced from replicon RNA resulting in amplified expression of foreign genes. The most preferred replicon gene arrangement places the foreign gene at the extreme 3' end of the genome where the viral structural protein is normally encoded. See FIG. 4. This position for the foreign gene at the extreme 3' end of the genome, as depicted in FIG. 4, is critical for high level expression (Culver, J. N., et al., *Virology* (in press)). However, the protein coding sequences or other gene sequences located between the replication origins may be functional in any order.

Additional preferred embodiments of the replicon sequence include the use of regulatable promoters to control expression of the foreign gene and/or movement protein. One promoter for expression of a fusion protein containing the foreign protein or a series of subgenomic promoters may be employed. Self-cleaving ribozymes or a polyadenylation region may also be employed as the transcription termination regions.

The replicons are generated in vivo in plants through transcription of transgenes that are integrated into the host plant cell chromosome and through replication in the presence of a helper virus. The transgenes can be introduced into the host plant cell chromosome by known transformation methods using a variety of promoters. After the replicon has been introduced into the host, the resulting transgenic plants are grown to an optimized stage at which point a helper virus strain is added. The replicons are then amplified by the introduced helper virus and the foreign gene is expressed.

The foreign gene product coded for and expressed by the replicon can be a very wide variety of RNA or proteins products and include, for example, antisense and ribozyme RNA, regulatory enzymes, and structural, regulatory and therapeutic proteins that may be expressed in their native form or as gene fusions. Typical therapeutic proteins include members of the interleukin family of proteins and colony stimulating factors such as CSF-G, CSF-GM and CSF-M. It is understood, however, that any therapeutic protein can be coded for and expressed in the instant invention.

If expression of the foreign gene results in the accumulation of a protein or other material in the plant tissues, that resulting product may be harvested once the desired concentration of that product is achieved. Significant quantities of recombinant proteins, nucleic acids or other metabolites can be inexpensively produced using this procedure. The low level of expression and wide variation that is observed in transgenic organisms chromosomally transformed with the same construct (a phenomenon attributed to "position effects"), is avoided by this method. RNA-based amplification is not critically dependent on initial transcript amounts. There is also no theoretical limit to the number of genes that can be amplified at the RNA level. The target gene remains "off" before amplification because subgenomic mRNA is only produced during viral replication. Therefore this approach might be particularly appropriate for controlling complex biochemical pathways or producing products that are toxic to the plant. It would be feasible for example, to overexpress critical enzymes in a pathway and simultaneously down-regulate other genes by amplifying antisense RNA only after inoculation with a helper virus. These types of manipulations are not possible using existing or proposed technologies for chromosomal transformation of plants or plant cell cultures or by using prior art viral vectors.

DESCRIPTION OF THE PREFERRED EMBODIMENTS

The following examples further illustrate the present invention.

EXAMPLE 1

Construction of a transgene for expression of recombinant messenger RNA

Construction of a transgene derived from TMV is set forth herein. The wild type TMV genome is set forth in FIG. 1. The construction of DNA plasmids containing the 5' replication origin fused to the CaMV 35S promoter are described in (Ow, D. W., et al., *Science* 234:856–859 (1986)) and the 3' replication origin fused to a ribozyme termination region are described by Turpen, T. H., Ph.D. Dissertation, University of California, Riverside, pp. 88–105 (1992).

The substitution of the coat protein gene for the coding sequence of CAT is described in Dawson, et al., *Phytopathol.* 78:783–789 (1988).

Previously disclosed plasmids, pBGC43, pBGC44, pBGC75 (Turpen, T. H., Ph.D. Disertation, University of California, Riverside, pp. 88–136 (1992)) and pTMVS3CAT28 (Dawson, et al., *Phytopathol.* 78:783–789 (1988)) are used as precursors for the construction of the desired transgene for synthesis of replicon RNA (FIG. 5). Construction of plasmids pBGC43, pBGC44, pBGC75 are described in Table 1 taken from Turpen, T. H., Ph.D. Disertation, University of California, Riverside, pp. 92, 112 (1992). Construction of plasmids pBGC43, pBGC44, pBGC75 and pTMVS3CAT28 are also discussed below.

Preparation of pTMVS3-CAT-28 pTMVS3-CAT-28 containing a substitution of the chloramphenicol acetyltransferase (CAT) gene for the coat protein gene was constructed as follows. The CAT gene was removed from pCM1 (Pharmacia) with SalI and ligated into XhoI-cleaved pTMVS3–28. pTMVS3–28 was constructed by cloning genomic length TMV cDNA (6.4 kb) in pBR322 as described in Dawson W., et al., *Proc. Natl. Acad. Sci.* 83:1832–36, (1986). The CAT construction produced pTMVS3-CAT-28 from which the mutant cp S3-CAT-28 was transcribed. Correct sequence and orientation were confirmed by sequencing. *Gene Anal. Technol.* 2:89–94.

Preparation of DBGC43 pTK49 was constructed by cloning the 1.4 kb PstI-HindIII fragment of TMV cDNA in pUC19 as described by Dawson, W., et al., *Proc. Natl. Acad. Sci.* 83:1832–36 (1986). The 1.4 kb PstI-HindIII from pTK49 was recloned into pUC19 to form pTT1. The 1.6 kb HindIII-BamHI fragment from pDO432 described in Ow et al., *Science* 234:856–59, (1986) was cloned into pTT1. NotI linkers were added at the HindIII site of the fragment and the EcoRI site of the vector. pTT3 was constructed by digesting pTT2 with PstI-BamHI and mung bean nuclease to position the 35S promoter at the 5' end of TMV cDNA. The 1.9 kb NotI-SmaI fragment of pTT3 was cloned into pBStKs+ to form pBGC43.

Preparation of pBGC44

The 1.4 kb SalI-HindIII fragment from pTT1 was cloned into pstSk- to form pBGC8. The 3.6 kb HindIII fragment from pTMV204 disclosed in Dawson, et al., *Proc. Natl. Acad. Sci.* 83:1832–36, (1986) was cloned into pBGC8 to form pBGC9. The 4.8 kb SmaI-PstI fragment from pBGC9 was cloned into pBGC43 (described above) to form pBGC44.

Preparation of pBGC 75

The 2.1 kb EcoRI-PstI fragment from pTMV204 described in Dawson, W., et al., *Proc. Natl. Acad. Sci.* 83:1832–36, (1986) was cloned into pBstSk- to form pBGC11. The 3.6 HindIII fragment from pTMV204 was cloned into pBGC11 to form pBGC14. The 0.4 kb NcoI-PstI fragment of pTMVcpS3–28 (0.5 kb coat protein deletion of pTMV304, described in Dawson, W., et al. *Phytopathology* 78:783–789) was substituted for the 0.9 kb NcoI-PstI fragment of pGC14 to form pGC15. pBGC19 was formed by deleting the 0.03 kb KpnI-HindIII polylinker region of pBGC14.

pBGC70 was formed by cloning a 0.05 kb synthetic ApaI-PstI ribozyme encoding fragment into pBstSk+. pBGC72 was formed by deleting the 3.5 kb ClaI fragment from pBGC19. pBGC73 was formed by cloning the 0.05 kb ApaI-PstI fragment of pBGC70 into pBGC72. pBGC74 was formed by substituting the 0.1 kb ClaI-NsiI fragment of pBGC15 for the 0.5 kb ClaI-NsiI fragment of pBGC73. The 3.5 kb ClaI fragment of pBGC19 was cloned into pBGC74 to form pBGC75.

TABLE 1

| Designation | Relevant Characteristics | Source or Reference |
|---|---|---|
| *E. coli* | | |
| JM109 | recA1, endA1, gyrA96, thi-, hsdR17($r_{K-}$, $m_{K+}$), supE44, relA1, A(kac-proAB) , [F traD36, proAB, lacI$^q$ZΔM15] | Yanish-Perron et al. Gene 33:103–199 (1985) |
| HB101 | hsdS20($r_{B-}$, $m_{B-}$), supE44, ara14, gelK2, lecY1, proA2, rspL20, xyl-5, mtl-1 recA13 | Sambrook et al. Molecular Cloning: A Laboratory Manual Cold Spring Harbor Laboratory (1989) |
| GJ23 | General plasmid mobilizing strain containing pGJ28 and pR64drd11 | Van Haute et al. EMBOJ. 2:411–417 (1983) |
| *A. tumefaciens* | | |
| C58C1 | Rif$^r$ derivative of strain C58 containing pGV3850 | Zambryski et al. EMBOJ. 2:2143–2150 (1983) |
| A. t.-17 | TMV transfection strain containing pGV3850::pBGC17 | Turpen, T.H., Ph.D. Dissertation, University of California, Riverside, pp. 106–132 (1992) |
| A. t.-46 | TMV transfection strain containing pGV3850::pBGC46 | Turpen, T.H., Ph.D. Dissertation, University of California, Riverside, pp. 106–132 (1992) |
| A. t.-49 | TMV transfection strain containing pGV3850::pBGC49 | Turpen, T.H., Ph.D. Dissertation, University of California, Riverside, pp. 106–132 (1992) |
| A. t.-77 | TMV transfection strain containing pGV3850::pBGC77 | Turpen, T.H., Ph.D. Dissertation, University of California, Riverside, pp. 88– |
| Plasmids | | |
| pBstSK/pBstKS | *E. coli* cloning plasmids, pBluescript (+/−) | Stratagene, La Jolla, California |
| pUC18/pUC19 | *E. coli* cloning plasmids | Yanish-Perron et al. Gene 33:103–199 (1985) |
| pT7/T3α19 | *E. coli* cloning plasmid | BRL, Gaithersburg, MD |
| pTK49 | 1.4 kb PstI-HindIII fragment of TMV cDNA in pUC19 | Dawson et al. Proc.Natl.Acad. Sci.U.S.A. 83:1832–1836 (1986) |
| pTMV204 | Genomic length TMV cDNA (6.4 kb) in pBR322 | Dawson, et al. Proc.Natl.Acad. Sci.U.S.A. 83:1832–1836 (1986) |
| pTMV212 | Genomic length TMV cDNA in pT7/T3α19 | Dawson, unpublished |
| pTMVcpS3-28 | Coat protein deletion (0.5 kb) mutant of pTMV204 | Dawson et al. Phytopathology 78:783–789 (1988) |
| pAP2034 | pBR322-_sed selection-expression vector for plant transformation, Cb$^r$, Sp$^r$, Kn$^r$ | Velton et al. NucleicAcidsRes. 13:6981–6998 (1985) |
| pDO432 | Source of restriction site modified 35S promoter | Ow et al. Science 234:856–859 (1986) |
| pTT1 | 1.4 kb PstI-HindIII fragtnent from pTK49 cloned in pUC19 | Turpen, T.H., Ph.D. Dissertation, University of California, Riverside, pp. 106–132 (1992) |
| pTT2 | 1.6 kb HindIII-bamHI fragment from pDO432 cloned | Turpen, T.H., Ph.D. |

TABLE 1-continued

| Designation | Relevant Characteristics | Source or Reference |
| --- | --- | --- |
| | in pTT1, NotI linkers added at KindIII site of fragment and EcoRI site of vector | Dissertation, University of California, Riverside, pp. 106–132 (1992) |
| pTT3 | PstI-BamHI + mung bean nuclease deletion of PTT2 positioning 35S promoter at 5'-end of TMV cDNA | Turpen, T.H., Ph.D. Dissertation, University of California, Riverside, pp. 106–132 (1992) |
| pBGC6 | 0.2 kb XhoI-PstI fragment from PTT1 cloned in pBstKS+ | Turpen, T.H., Ph.D. Dissertation, University of California, Riverside, pp. 106–132 (1992) |
| pBGC8 | 1.4 kb SalI-HindIII fragment from PTTT cloned in pBstSK– | Turpen, T.H., Ph.D. Dissertation, University of California, Riverside, pp. 106–132 (1992) |
| pBGC9 | 3.6 kb HindIII fragrnent from pTMV204 cloned in pBGC8 | Turpen, T.H., Ph.D. Dissertation, University of California, Riverside, pp. 106–132 (1992) |
| pBGC11 | 2.1 kb EcoRI-PstI fragment from pTMV204 cloned in pBstSK– | Turpen, T.H., Ph.D. Dissertation, University of California, Riverside, pp. 106–132 (1992) |
| pBGC14 | 3.6 kb HindIII fragment from pTMV204 cloned in pBGC11 | Turpen, T.H., Ph.D. Dissertation, University of California, Riverside, pp. 106–132 (1992) |
| pBGC15 | 0.4 kb NcoI-PstI of pTMVcpS3-28 substituted for 0.9 kb NcoI-PstI fragment of pBGC14 | Turpen, T.H., Ph.D. Dissertation, University of California, Riverside, pp. 88–105 (1992) |
| pBGC16 | 3.3 kb SalI-BamHI fragment of pBGC9 cloned in pAP2034 | Turpen, T.H., Ph.D. Dissertation, University of California, Riverside, pp. 106–132 (1992) |
| pBGC17 | Full length wtTMV cDNA in pAP2034 | Turpen, T.H., Ph.D. Dissertation, University of California, Riverside, pp. 106–132 (1992) |
| pBGC19 | 0.03 kb KpnI-HindIII polylinker deletion of pBGC14 | Turpen, T.H., Ph.D. Dissertation, University of California, Riverside, pp. 106–132 (1992) |
| pBGC43 | 1.9 kb NotI-SmaI fragment from pTT3 cloned in pBstKS+ | Turpen, T.H., Ph.D. Dissertation, University of California, Riverside, pp. 106–132 (1992) |
| pBGC44 | 4.8 kb SmaI-PstI fragment of pBGC9 cloned in pBGC43 | Turpen, T.H., Ph.D. Dissertation, University of California, Riverside, pp. 106–132 (1992) |
| pBGC45 | 4.3 kb BglII-BamHI fragment of pBGC44 cloned in the BamHI site of pAP2034 | Turpen, T.H., Ph.D. Dissertation, University of California, Riverside, pp. 106–132 (1992) |
| pBGC46 | 3.1 kb BamHI fragment of pBGC44 cloned in the BamHI site of pAP2043 | Turpen, T.H., Ph.D. Dissertion, University of California, Riverside, pp. 106–132 (1992) |
| pBGC49 | 2.6 kb BamHI fragment of pBGC14 cloned in the BamHI site of pBGC45 | Turpen, T.H., Ph.D. Dissertion, University of California, Riverside, pp. 106–132 (1992) |
| pBGC70 | 0.05 kb synthetic ApaI-PstI ribozyme encoding fragment cloned in pBstSK+ | Turpen, T.H., Ph.D. Dissertion, University of California, Riverside, pp. 88–105 (1992) |
| pBGC72 | 3.5 kb ClaI deletion of pBGC19 | Turpen, T.H., Ph.D. Dissertation, University of California, Riverside, pp. 88–105 (1992) |
| pBGC73 | 0.05 kb ApaI-PstL fragment of pBGC70 cloned in pBGC72 | Turpen, T.H., Ph.D. Dissertation, University of California, Riverside, pp.88–105 (1992) |
| pBGC74 | 0.1 kb ClaI-NsiI fragment of pBGC15 substituted for 0.5 kb ClaI-NsiI fragment of pBGC73 | Turpen, T.H., Ph.D. Dissertation, University of |

TABLE 1-continued

| Designation | Relevant Characteristics | Source or Reference |
| --- | --- | --- |
| | | California, Riverside, pp. 88–105 (1992) |
| pBGC75 | 3.5 kb ClaI fragment of pBGC19 cloned into pBGC74 | Turpen, T.H., Ph.D. Dissertation, University of California, Riverside, pp. 88–105 (1992) |
| pBGC77 | 2.7 kb BamHI fragment of pBGC75 cloned into pBGC45, 35S promoter plus full length cp-TMV cDNA in pAP2034 with ribozyme self-cleaving fragment at 3'-terminus | Turpen, T.H., Ph.D. Dissertation, University of California, Riverside, pp. 88–105 (1992) |

Figure 5:
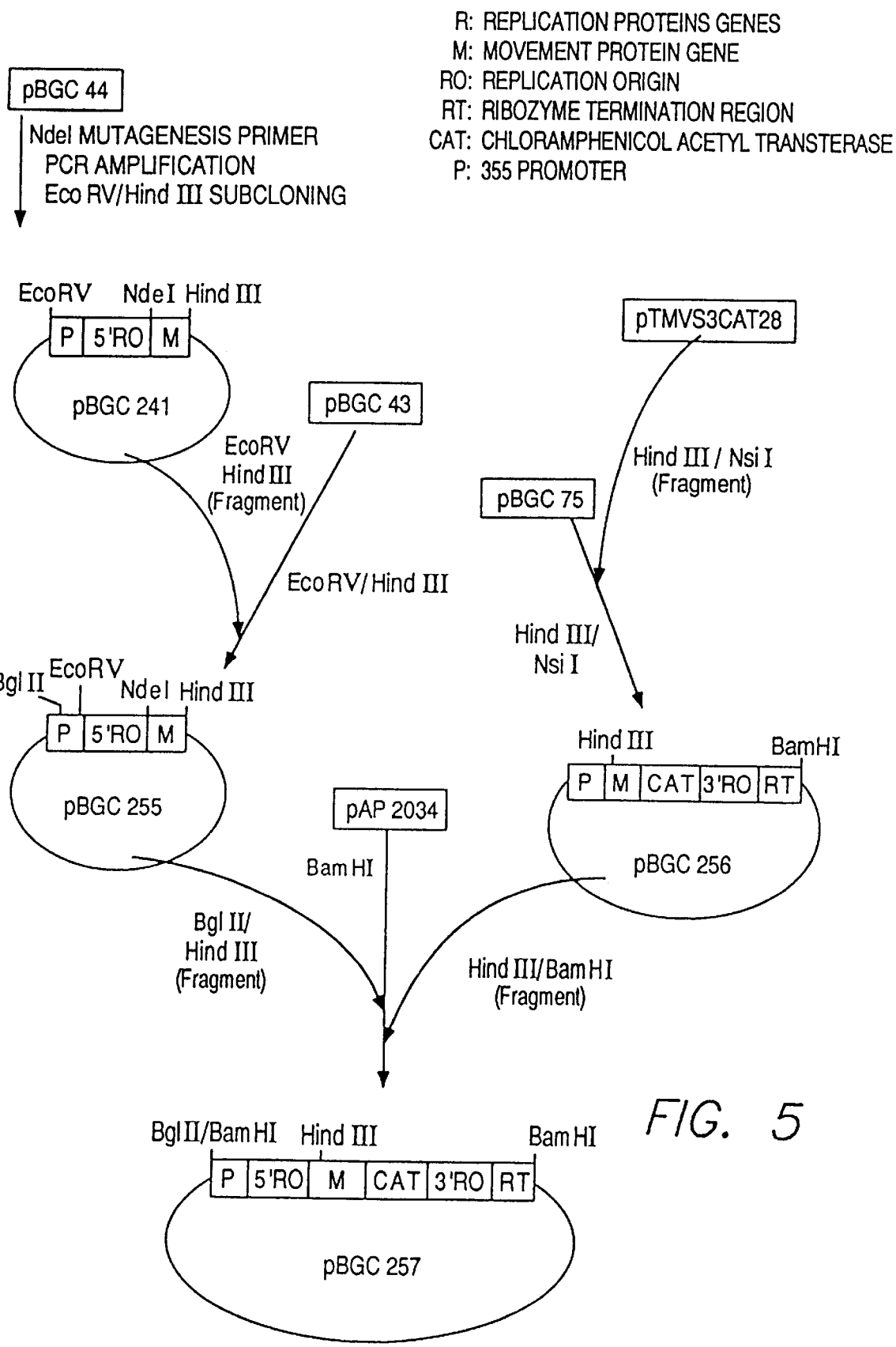
FIG. 5 depicts the construction of a transgene for the synthesis of a replicon encoding Chloramphenicol Acetyl-transferase (CAT) in an *Agrobacterium* transformation vector.

In this construction, it is desired to place the 30-kDA movement protein gene at precisely the same position as the replicase gene (relative to 5' replication origin in the wild type TMV genome, See FIG. 5). To accomplish this, a NdeI site is introduced at the start codon of each gene by PCR-based mutagenesis using synthetic primers and unique adjacent cloning sites. A 270 bp mutagenesis product containing the internal NdeI site from the PCR primer is subcloned using the EcoRV site in the cauliflower mosaic virus 35S promoter and the HindIII site in the 30-kDa protein gene. The ligation product is then sequence verified.

The 3' segment of the replicon, containing the CAT gene will be placed adjacent to the 3'-ribozyme as a HindIII-NsiI fragment from the transient TMV vector pTMVS3CAT28 (FIG. 5). In the final cloning step, the 5' portion of the transgene and the 3' portion will be subcloned into the unique BamHI site of the plant transformation vector pAP2034 (Velton and Schell, NAR 13:6981–6998 (1985) as a BglII-BamHI fragment described previously (Turpen, T. H., Ph.D. Dissertation, University of California, Riverside, pp. 88–132 (1992)). The sequence of the replicon RNA, produced by host transcription, RNA processing, and replication in the presence of a helper virus, is given in FIG. 6. Thus, the foreign gene (CAT) is placed on a RNA viral replicon, under control of the coat protein subgenomic promoter for messenger RNA synthesis (located at the 3' end of the movement protein gene).

EXAMPLE 2
Transformation of Plants.

In one embodiment of this invention, Agrobacterium tumefaciens is used for insertion of this sequence into the plant chromosome as described previously (Turpen, T. H., Ph.D. Dissertation, University of California, Riverside, pp. 106–132 (1992)). The transformation vector pAP2034 is a cointegrating type Agrobacterium vector. pAP2034 containing the transcription unit for the production of replicon RNA is mobilized into A. tumefaciens by conjugation using the helper strain GJ23 (Van Haute, E., Joos, et al., EMBO J. 2:411–417 (1983)). Transconjugants are selected and the structure of the cointegrate between donor plasmid and the disarmed Ti plasmid pGV3850 (Zambryski, P., et al., EMBO J. 2:2143–2150 (1983)) is confirmed by Southern blot hybridization. A correct homologous recombination event places the transgene construct between the T-DNA borders.

Axenic leaf segments of N. tabacum cv. Xanthi are treated (Horsch, R. B., et al., Leaf disc transformation, Plant molecular biology manual. (S. B. Gelvin, R. A. Schilperoort, and D. P. S. Verma, eds.), Kluwer Academic Publishers, Dordrecht, The Netherlands, pp. A5:1–9 (1988)) in the following sequence: day 1; leaf segments are dipped in A. tumefaciens liquid culture and placed on regeneration media (RM), day 3; explants are transferred to RM supplemented with cefotaxime (500 µg/ml), day 5; explants are transferred to RM/cefotaxime (500 µg/ml)+kanamycin (100 µg/ml), day 30–40; shoots excised and placed onto rooting media containing cefotaxime (500 µg/ml) and kanamycin (100 µg/ml). Cultures are maintained under continuous fluorescent light (Sylvania GTE, Gro-Lux WS) at 20° C.

Hardened plants are grown in commercial potting soil (Cascade Forest Products Inc., Arcata, Calif.) at a temperature of 21–29° C., with a controlled release fertilizer (Osmocote, 14-14-14) using natural light (Vacaville, Calif.) supplemented with fluorescent light on a 16 hr day length in an indoor greenhouse. The antibiotic resistance trait carried in transgenic lines is scored by germinating seedlings in sterile agar in the presence of 100 µg/ml kanamycin (Dunsmuir, P., et al., Stability of introduced genes and stability of expression, Plant molecular biology manual. (S. B. Gelvin, R. A. Schilperoort, and D. P. S. Verma, eds.), Kluwer Academic Publishers, Dordrecht, The Netherlands, pp. C1:1–17 (1988)).

EXAMPLE 3.
Production of Replicon RNA in the presence of Helper Virus.

The sequence of the replicon RNA, produced by host transcription, RNA processing, and replication in the presence of a helper virus, is given in FIG. 6. Tobamoviruses with mutations or naturally occurring variation in the 30-kDa protein gene are deficient in cell-to-cell movement on specific host species. Transgenic plants or alternate hosts can complement this defect. It will be appreciated to those skilled in the art that there are numerous methods of producing helper tobamoviruses by genetic engineering or by mutagenesis in addition to those helper variants or host species combinations occurring naturally. Likewise, methods for producing transgenic plants which express 30 kDa protein and which complement defective 30 kDa containing viruses have been published. For example, movement deficient helper viruses can be synthesized by transcription of TMV with known mutations for the production of RNA inoculum. Transgenic plants expressing the 30-kDa protein complement this defect (Deom, C. M., et al., Science 237:389–394 (1987)). Therefore, large quantities of a helper virus can be propagated. In one embodiment of this invention, a 30-kDa protein frameshift mutant, having a single base pair deletion at position 4931 thereby creating a EcoRV site in the cDNA, is used as helper virus. Transgenic tobacco (~100 plants) are regenerated containing this replicon transgene construction and assayed for CAT activity in the presence and absence of helper viruses using procedures described (Shaw, W. V., Chloramphenicol acetyltransferase from chloramphenicol-resistant bacteria, Methods in Enzymology, Vol. 53, (S. Fleischer and L. Packer, eds.), pp. 737–755 (1975)). 200 mg of leaf tissue is macerated in assay buffer followed by the addition of 0.5 nM acetyl CoA and 0.1 uCi [$^{14}$C] chloramphenicol, incubation for 45 min at 37° C., extraction, resolution by thin-layer chromatography, and autoradiography.

While the invention of this patent application is disclosed by reference to the details of preferred embodiments of the invention, it is to be understood that this disclosure is intended in an illustrative rather than limiting sense, as it is contemplated that modifications will readily occur to those skilled in the art, within the spirit of the invention and the scope of the appended claims. It is further understood that the instant invention applies to all viruses infecting plants and plants generally and is not limited to those plasmids, viruses or plants described herein.

What is claimed is:

1. A system comprising:
   a replicon comprising:
   a plus sense, single-stranded RNA plant virus derived replication origin for replicating the replicon,
   a nucleic acid sequence non-native to the replicon encoding an RNA or protein product.
   the replicon not encoding for at least a plus sense, single stranded RNA plant virus replicase, and
   a plus sense, single-stranded RNA plant virus derived helper virus encoding;
   at least a plus sense, single stranded RNA plant virus replicase, and
   the helper virus not encoding at least a plus sense, single stranded RNA plant virus movement protein,
   wherein the replicon further encodes at least a plus sense, single stranded RNA plant virus movement protein, and
   wherein a DNA sequence of the replicon is integrated as a transgene into the chromosome of a host cell suitable for replicating the replicon.

2. The system of claim 1, wherein said nucleic acid sequence is located 5' to the 3' replication origin of the replicon.

3. The system of claim 1, wherein the viral movement protein is native to a tobamovirus.

4. The system of claim 3, wherein the DNA encoding the tobamovirus movement protein is located 3' to the replication origin of the replicon.

5. The system of claim 1, wherein the viral movement protein is native to a TMV.

6. The system of claim 5, wherein the DNA encoding the TMV movement protein is located 3' to the 5' replication origin of the replicon.

7. The system of claim 2, wherein said product is expressed systemically.

8. A transgenic plant containing a system comprising:
   a replicon comprising;
   a plus sense, single-stranded RNA plant virus derived replication origin for replicating the replicon,
   a nucleic acid cc non-native to the replicon encoding an RNA or protein product,
   the replicon not encoding for at least a plus sense, single stranded RNA plant virus replicase, and
   a plus sense, single-stranded RNA plant virus derived helper virus encoding;
   at least a plus sense, single stranded RNA plant virus replicase, and
   the helper virus not encoding at least a plus sense, single stranded RNA plant virus movement protein,
   wherein the replicon further encodes at least a plus sense, single stranded RNA plant virus movement protein, and
   wherein a DNA sequence of the replicon is integrated as a transgene into the chromosome of a host cell suitable for replicating the replicon.

9. The transgenic plant of claim 8, wherein the transgenic plant is suitable as a host for a tobamovirus.

10. The transgenic plant of claim 8, wherein the transgenic plant is suitable as a host for a TMV.

11. A method for expressing a protein in plants comprising:
   (a) integrating a transgene into a chromosome of a plant cell for transcribing the transgene, the transgene encoding for a replicon which comprises;
   a plus sense, single-stranded RNA plant virus derived replication origin for replicating the replicon,
   a nucleic acid sequence non-native to the replicon encoding an RNA or protein product,
   the replicon not encoding for at least a plus sense, single stranded RNA plant virus replicase,
   wherein a DNA sequence of the replicon is integrated as a transgene into the chromosome of a host cell for replicating the replicon, and
   (b) infecting the plant cell with a plus sense, single-stranded RNA plant virus derived helper virus encoding;
   at least a plus sense, single stranded RNA plant virus replicase, and
   the helper virus not encoding at least a plus sense, single stranded RNA plant virus movement protein, wherein the replicon further encodes at least a plus sense, single stranded RNA plant virus movement protein, and (c) expressing said nucleic acid sequence.

12. A method of claim 11, wherein the movement protein is native to tobamovirus.

13. A method of claim 11, wherein the movement protein is native to TMV.

14. A method for producing a primary or secondary metabolite accumulated in the tissues of a transfected plant comprising:
   (a) integrating a transgene into a chromosome of a host cell suitable for transcribing the transgene, the transgene encoding for a replicon which comprises:
      a plus sense single-stranded RNA plant virus derived replication origin for replicating the replicon,
      a nucleic acid sequence non-native to the replicon encoding an RNA or protein product,
      the replicon not encoding for at least a plus sense, single stranded RNA plant virus replicase, and
   (b) infecting the plant cell with a plus sense, single-stranded RNA plant virus derived helper virus encoding;
      at least a plus sense, single stranded RNA plant virus replicase, and
      the helper virus not encoding at least a plus sense, single stranded RNA plant virus movement protein wherein the replicon further encodes at least plus sense single stranded RNA plant virus movement protein,
   (c) expressing said nucleic acid sequence, and
   (d) producing a primary or secondary metabolite using the RNA or protein encoded by said nucleic acid sequence.

15. A method of claim 14, wherein the movement protein is native to tobamovirus.

16. A method of claim 14, wherein the movement protein is native to TMV.

17. A system comprising:
   a replicon comprising:
      a TMV-derived replication origin,
      at least one gene non-native to TMV encoding a product non-native to TMV, and
      a gene encoding a TMV-derived viral movement protein,
      wherein said replicon lacks a gene encoding a TMV-derived replicase; and
   a TMV helper virus lacking a functional gene encoding a viral movement protein, said TMV helper virus comprising a gene encoding a TMV replicase;
   wherein a DNA sequence of the replicon is integrated as a transgene in the chromosome of a tobacco cell.

18. A transgenic plant containing a system comprising:
   a replicon comprising:
      a TMV-derived replication origin,
      at least one gene non-native to TMV encoding a product non-native to TMV, and
      a gene encoding a TMV-derived viral movement protein,
      wherein said replicon lacks a gene encoding a TMV-derived replicase; and
   a TMV helper virus lacking a functional gene encoding a viral movement protein, said TMV helper virus comprising a gene encoding a TMV replicase, and
   wherein the replicon is integrated as a transgene in the chromosome of a tobacco plant cell.

19. A method for expressing a protein in plants comprising:
   (a) integrating a transgene into a chromosome of a tobacco cell, the transgene comprising a replicon comprising:
      a TMV-derived replication origin,
      at least one gene non-native to TMV encoding a product non-native to TMV, and
      a gene encoding a TMV-derived viral movement protein,
      wherein said replicon lacks a gene encoding a TMV-derived replicase; and
   (b) infecting the tobacco cell with a TMV helper virus, the TMV helper virus comprising:
      a gene encoding a TMV replicase, and lacking a functional gene encoding a viral movement protein.

20. A system comprising:
   a replicon comprising:
      a tobamovirus derived replication origin,
      a nucleic acid encoding an RNA or protein product that is non-native to the replicon,
      a tobamovirus viral movement protein gene,
      wherein the replicon lacks a tobamovirus viral replicase gene, and a helper virus encoding;
      a tobamovirus viral replicase gene, and
      wherein the helper virus lacks a tobamovirus viral movement protein gene, and
   wherein a DNA sequence of the replicon is integrated as a transgene in the chromosome of a plant cell, suitable as a host for a tobamovirus.

21. A system comprising:
   a replicon comprising:
      a TMV derived replication origin,
      a nucleic acid encoding an RNA or protein that is non-native to the replicon,
      a TMV viral movement protein gene,
      wherein the replicon lacks a TMV viral replicase gene, and a helper virus encoding;
      a TMV viral replicase gene, and
      wherein the helper virus lacks a TMV viral movement protein gene, and
   wherein a DNA sequence of the replicon is integrated as a transgene in the chromosome of a plant cell, suitable as a host for TMV.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 1825
      (B) TYPE: nucleic acid
      (C) STRANDEDNESS: single
      (D) TOPOLOGY: linear (ii) MOLECULE TYPE: RNA (episomal), peptide
      (A) DESCRIPTION: Peptide encodes for TMV 30kDa movement protein (268 residues) and CAT (204 residues).

(iii) HYPOTHETICAL: NO (iv) ANTI-SENSE: NO (vi) ORIGINAL SOURCE:
      (A) ORGANISM: Tobacco Mosaic Virus (vii) IMMEDIATE SOURCE:
      (B) CLONE:

(ix) FEATURE:

(xi) SEQUENCE DESCRIPTION: SEQ ID NO: 1:

```
GUAUUUUAC AACAAUUACC AACAACAACA AACAACAAAC AACAUUACAA UUACUAUUUA        60

CAAUUACAU AUG GCU CUA GUU GUU AAA GGA AAA GUG AAU AUC AAU             105
           Met Ala Leu Val Val Lys Gly Lys Val Asn Ile Asn
                              5                   10

GAG UUU AUC GAC CUG ACA AAA AUG GAG AAG AUC UUA CCG UCG AUG           150
Glu Phe Ile Asp Leu Thr Lys Met Glu Lys Ile Leu Pro Ser Met
         15                  20                  25

UUU ACC CCU GUA AAG AGU GUU AUG UGU UCC AAA GUU GAU AAA AUA           195
Phe Thr Pro Val Lys Ser Val Met Cys Ser Lys Val Asp Lys Ile
             30                  35                  40

AUG GUU CAU GAG AAU GAG UCA UUG UCA GAG GUG AAC CUU UUU AAA           240
Met Val His Glu Asn Glu Ser Leu Ser Glu Val Asn Leu Phe Lys
                 45                  50                  55

GGA GUU AAG CUU AUU GAU AGU GGA UAC GUC UGU UUA GCC GGU UUG           285
Gly Val Lys Leu Ile Asp Ser Gly Tyr Val Cys Leu Ala Gly Leu
                     60                  65                  70

GUC GUC ACG GGC GAG UGG AAC UUG CCU GAC AAU UGC AGA GGA GGU           330
Val Val Thr Gly Glu Trp Asn Leu Pro Asp Asn Cys Arg Gly Gly
                         75                  80                  85

GUG AGC GUG UGU CUG GUG GAC AAA AGG AUG GAA AGA GCC GAC GAG           375
Val Ser Val Cys Leu Val Asp Lys Arg Met Glu Arg Ala Asp Glu
                             90                  95             100

GCC ACU CUC GGA UCU UAC UAC ACA GCA GCU GCA AAG AAA AGA UUU           420
Ala Thr Leu Gly Ser Tyr Tyr Thr Ala Ala Ala Lys Lys Arg Phe
                                 105                 110             115

CAG UUC AAG GUC GUU CCC AAU UAU GCU AUA ACC ACC CAG GAC GCG           465
```

|     |     |     |     |     |     |     |     |     |     |     |     |      |
|-----|-----|-----|-----|-----|-----|-----|-----|-----|-----|-----|-----|------|
| Gln | Phe | Lys | Val | Val | Pro | Asn | Tyr | Ala | Ile | Thr | Thr | Gln Asp Ala |
|     | 120 |     |     |     | 125 |     |     |     |     | 130 |     |      |

```
AUG AAA AAC GUC UGG CAA GUU UUA GUU AAU AUU AGA AAU GUG AAG          510
Met Lys Asn Val Trp Gln Val Leu Val Asn Ile Arg Asn Val Lys
    135                 140                 145

AUG UCA GCG GGU UUC UGU CCG CUU UCU CUG GAG UUU GUG UCG GUG          555
Met Ser Ala Gly Phe Cys Pro Leu Ser Leu Glu Phe Val Ser Val
    150                 155                 160

UGU AUU GUU UAU AGA AAU AAU AUA AAA UUA GGU UUG AGA GAG AAG          600
Cys Ile Val Tyr Arg Asn Asn Ile Lys Leu Gly Leu Arg Glu Lys
    165                 170                 175

AUU ACA AAC GUG AGA GAC GGA GGG CCC AUG GAA CUU ACA GAA GAA          645
Ile Thr Asn Val Arg Asp Gly Gly Pro Met Glu Leu Thr Glu Glu
    180                 185                 190

GUC GUU GAU GAG UUC AUG GAA GAU GUC CCU AUG UCG AUC AGG CUU          690
Val Val Asp Glu Phe Met Glu Asp Val Pro Met Ser Ile Arg Leu
    195                 200                 205

GCA AAG UUU CGA UCU CGA ACC GGA AAA AAG AGU GAU GUC CGC AAA          735
Ala Lys Phe Arg Ser Arg Thr Gly Lys Lys Ser Asp Val Arg Lys
    210                 215                 220

GGG AAA AAU AGU AGU AAU GAU CGG UCA GUG CCG AAC AAG AAC UAU          780
Gly Lys Asn Ser Ser Asn Asp Arg Ser Val Pro Asn Lys Asn Tyr
    225                 230                 235

AGA AAU GUU AAG GAU UUU GGA GGA AUG AGU UUU AAA AAG AAU AAU          825
Arg Asn Val Lys Asp Phe Gly Gly Met Ser Phe Lys Lys Asn Asn
    240                 245                 250

UUA AUC GAU GAU GAU UCG GAG GCU ACU GUC GCC GAA UCG GAU UCG          870
Leu Ile Asp Asp Asp Ser Glu Ala Thr Val Ala Glu Ser Asp Ser
    255                 260                 265

UUU UAA AUACGCUCGA CGAGAUUUUC AGGAGCUAAG GAAGCUAAA AUG GAG AAA       924
Phe *                                                  Met Glu Lys

AAA AUC ACU GGA UAU ACC ACC GUU GAU AUA UCC CAA UCG CAU CGU          969
Lys Ile Thr Gly Tyr Thr Thr Val Asp Ile Ser Gln Ser His Arg
      5                  10                  15

AAA GAA CAU UUU GAG GCA UUU CAG UCA GUU GCU CAA UGU ACC UAU         1014
Lys Glu His Phe Glu Ala Phe Gln Ser Val Ala Gln Cys Thr Tyr
     20                  25                  30

AAC CAG ACC GUU CAG CUG GAU AUU ACG GCC UUU UUA AAG ACC GUA         1059
Asn Gln Thr Val Gln Leu Asp Ile Thr Ala Phe Leu Lys Thr Val
     35                  40                  45

AAG AAA AAU AAG CAC AAG UUU UAU CCG GCC UUU AUU CAC AUU CUU         1104
Lys Lys Asn Lys His Lys Phe Tyr Pro Ala Phe Ile His Ile Leu
     50                  55                  60

GCC CGC CUG AUG AAU GCU CAU CCG GAA UUC CGU AUG GCA AUG AAA         1149
Ala Arg Leu Met Asn Ala His Pro Glu Phe Arg Met Ala Met Lys
     65                  70                  75

GUU UUC CAU GAG CAA ACU GAA ACG UUU UCA UCG CUC UGG AGU GAA         1194
Val Phe His Glu Gln Thr Glu Thr Phe Ser Ser Leu Trp Ser Glu
     80                  85                  90

UAC CAC GAC GAU UUC CGG CAG UUU CUA CAC AUA UAU UCG CAA GAU         1239
Tyr His Asp Asp Phe Arg Gln Phe Leu His Ile Tyr Ser Gln Asp
     95                 100                 105

GUG GCG UGU UAC GGU GAA AAC CUG GCC UAU UUC CCU AAA GGG UUU         1284
Val Ala Cys Tyr Gly Glu Asn Leu Ala Tyr Phe Pro Lys Gly Phe
    110                 115                 120

AUU GAG AAU AUG UUU UUC GUC UCA GCC AAU CCC UGG GUG AGU UUC         1329
Ile Glu Asn Met Phe Phe Val Ser Ala Asn Pro Trp Val Ser Phe
    125                 130                 135

ACC AGU UUU GAU UUA AAC GUG GCC AAU AUG GAC AAC UUC UUC GCC         1374
Thr Ser Phe Asp Leu Asn Val Ala Asn Met Asp Asn Phe Phe Ala
```

-continued

```
         140                 145                 150
CCC GUU UUC ACC AUG GGC AAA UAU UAU ACG CAA GGC GAC AAG GUG      1419
Pro Val Phe Thr Met Gly Lys Tyr Tyr Thr Gln Gly Asp Lys Val
    155                 160                 165

CUG AUG CCG CUG GCG AUU CAG GUU CAU CAU GCC GUC UGU GAU GGC      1464
Leu Met Pro Leu Ala Ile Gln Val His His Ala Val Cys Asp Gly
    170                 175                 180

UUC CAU GUC GGC AGA AUG CUU AAU GAA UUA CAA CAG UAC UGC GAU      1509
Phe His Val Gly Arg Met Leu Asn Glu Leu Gln Gln Tyr Cys Asp
    185                 190                 195

GAG UGG CAG GGC GGG GCG UAA UUUUUUUAAG GCAGUUAUUG GUGCCCUUA AAC  1562
Glu Trp Gln Gly Gly Ala *
    200

GCCUGGUGCU ACGCCUGAAU AAGUGAUAAU AAGCGGAUGA AUGGCAGAAA UUCGUCGAGG  1622

GUAGUCAAGA UGCAUAAUAA AUAACGGAUU GUGUCCGUAA UCACACGUGG UGCGUACGAU  1682

AACGCAUAGU GUUUUUCCCU CCACUUAAAU CGAAGGGUUG UGUCUUGGAU CGCGCGGGUC  1742

AAAUGUAUAU GGUUCAUAUA CAUCCGCAGG CACGUAAUAA AGCGAGGGGU UCGAAUCCCC  1802

CCGUUACCCC CGGUAGGGGC CCA                                        1825
```